(12) United States Patent
Liang et al.

(10) Patent No.: US 11,264,139 B2
(45) Date of Patent: Mar. 1, 2022

(54) METHOD AND SYSTEM FOR ADJUSTING INTERACTIVE 3D TREATMENT ZONE FOR PERCUTANEOUS TREATMENT

(71) Applicant: EDDA TECHNOLOGY, INC., Princeton, NJ (US)

(72) Inventors: Cheng-Chung Liang, West Windsor, NJ (US); Guo-Qing Wei, Plainsboro, NJ (US); Li Fan, Belle Mead, NJ (US); Jianzhong Qian, Princeton Junction, NJ (US); Xiaolan Zeng, Princeton, NJ (US)

(73) Assignee: EDDA TECHNOLOGY, INC., Princeton, NJ (US)

( * ) Notice: Subject to any disclaimer, the term of this patent is extended or adjusted under 35 U.S.C. 154(b) by 432 days.

(21) Appl. No.: 14/926,559

(22) Filed: Oct. 29, 2015

(65) Prior Publication Data
US 2016/0058521 A1 Mar. 3, 2016

Related U.S. Application Data

(63) Continuation-in-part of application No. 12/275,699, filed on Nov. 21, 2008.
(Continued)

(51) Int. Cl.
*G16H 50/50* (2018.01)
*A61B 34/10* (2016.01)
(Continued)

(52) U.S. Cl.
CPC ............. *G16H 50/50* (2018.01); *A61B 34/10* (2016.02); *G06T 19/00* (2013.01); *G16Z 99/00* (2019.02);
(Continued)

(58) Field of Classification Search
CPC .................................................. G06F 19/3437
See application file for complete search history.

(56) References Cited

U.S. PATENT DOCUMENTS 6,064,904 A * 5/2000 Yanof ..................... A61B 90/10
  600/414
6,426,745 B1 * 7/2002 Isaacs ................. G06F 3/04845
  345/419
(Continued)

FOREIGN PATENT DOCUMENTS

CN  101859341 A  10/2010
CN  101877996 A  11/2010
(Continued)

OTHER PUBLICATIONS

International Search Report and Written Opinion dated Feb. 4, 2016 in International Application PCT/US2015/058441.
(Continued)

*Primary Examiner* — William D Ermlick
(74) *Attorney, Agent, or Firm* — Venable LLP

(57) ABSTRACT

The present teaching relates to surgical procedure planning. In one example, at least one 3D object contained in a 3D volume is rendered on a display screen. The at least one 3D object includes a 3D object corresponding to an organ. First information related to a 3D pose of a surgical instrument positioned with respect to the at least one 3D object is received from a user. A 3D representation of the surgical instrument is rendered in the 3D volume based on the first information. Second information related to a setting of the surgical instrument is received from the user. A 3D treatment zone in the 3D volume with respect to the at least one 3D object is estimated based on the first and second information. The 3D treatment zone in the 3D volume is visualized on the display screen. Controls associated with the 3D representation of the surgical instrument and/or the 3D treatment zone
(Continued)

are provided to facilitate the user to dynamically adjust the 3D treatment zone via the controls.

18 Claims, 23 Drawing Sheets

Related U.S. Application Data

(60) Provisional application No. 60/989,580, filed on Nov. 21, 2007, provisional application No. 62/073,420, filed on Oct. 31, 2014.

(51) Int. Cl.
*G06T 19/00* (2011.01)
*G16Z 99/00* (2019.01)

(52) U.S. Cl.
CPC ... *A61B 2034/102* (2016.02); *A61B 2034/105* (2016.02); *G06T 2210/41* (2013.01)

(56) References Cited

U.S. PATENT DOCUMENTS

| | | | |
|---|---|---|---|
| 7,236,618 B1* | 6/2007 | Chui | G06F 3/016 382/128 |
| 7,315,304 B2 | 1/2008 | Liang et al. | |
| 8,055,323 B2* | 11/2011 | Sawyer | A61N 5/1049 600/407 |
| 8,643,675 B2* | 2/2014 | Mlejnek | G06T 7/0012 345/632 |
| 8,675,022 B2* | 3/2014 | Liang | G06T 17/00 345/653 |
| 9,542,068 B2* | 1/2017 | Tai | G06F 3/04883 |
| 9,743,993 B2* | 8/2017 | Zhang | G16H 50/50 |
| 10,025,884 B1* | 7/2018 | Samah | G06F 30/23 |
| 2001/0031920 A1 | 10/2001 | Kaufman | |
| 2003/0032878 A1* | 2/2003 | Shahidi | A61B 5/06 600/429 |
| 2004/0009459 A1* | 1/2004 | Anderson | G06F 19/3481 434/262 |
| 2004/0015070 A1* | 1/2004 | Liang | G06F 19/3481 600/407 |
| 2004/0233223 A1* | 11/2004 | Schkolne | G06F 3/0346 345/621 |
| 2005/0015005 A1 | 1/2005 | Kockro | |
| 2005/0043609 A1 | 2/2005 | Murphy et al. | |
| 2005/0174347 A1 | 8/2005 | Visser | |
| 2006/0020206 A1* | 1/2006 | Serra | A61B 8/00 600/447 |
| 2006/0142657 A1 | 6/2006 | Quaid | |
| 2006/0274885 A1* | 12/2006 | Wang | G06Q 50/22 378/65 |
| 2007/0073905 A1* | 3/2007 | Cynthia | A61F 9/00804 710/1 |
| 2007/0103464 A1 | 5/2007 | Kaufman | |
| 2007/0129626 A1* | 6/2007 | Mahesh | G16H 40/63 600/407 |
| 2007/0203545 A1* | 8/2007 | Stone | A61N 1/0529 607/59 |
| 2007/0239150 A1* | 10/2007 | Zvuloni | A61B 8/0833 606/21 |
| 2007/0248261 A1 | 10/2007 | Zhou et al. | |
| 2007/0279436 A1* | 12/2007 | Ng | G16H 50/50 345/624 |
| 2008/0275439 A1* | 11/2008 | Francischelli | A61B 18/1492 606/34 |
| 2009/0002366 A1* | 1/2009 | Kanitsar | A61B 6/032 345/419 |
| 2009/0036902 A1* | 2/2009 | DiMaio | A61B 34/10 606/130 |
| 2009/0124896 A1* | 5/2009 | Haras | A61B 18/14 600/427 |
| 2009/0142740 A1* | 6/2009 | Liang | A61B 34/10 434/262 |
| 2009/0221999 A1* | 9/2009 | Shahidi | A61B 18/18 606/33 |
| 2009/0253109 A1 | 10/2009 | Anvari et al. | |
| 2009/0287467 A1* | 11/2009 | Sparks | G16H 50/50 703/21 |
| 2009/0318804 A1* | 12/2009 | Avital | A61B 18/02 600/439 |
| 2010/0250209 A1* | 9/2010 | Pearson | A61B 18/1206 703/2 |
| 2010/0261526 A1 | 10/2010 | Anderson et al. | |
| 2010/0312095 A1* | 12/2010 | Jenkins | A61B 5/415 600/411 |
| 2011/0040547 A1* | 2/2011 | Gerber | A61N 1/37235 703/11 |
| 2011/0107270 A1* | 5/2011 | Wang | G06F 19/3481 715/850 |
| 2011/0170752 A1* | 7/2011 | Martin | G09B 23/285 382/128 |
| 2011/0208055 A1* | 8/2011 | Dalal | A61N 7/02 600/439 |
| 2012/0100517 A1* | 4/2012 | Bowditch | G09B 23/30 434/267 |
| 2012/0189998 A1* | 7/2012 | Kruecker | G09B 23/286 434/272 |
| 2012/0209106 A1 | 8/2012 | Liang et al. | |
| 2012/0237105 A1 | 9/2012 | Mielekamp | |
| 2012/0282583 A1* | 11/2012 | Thaler | G09B 23/28 434/267 |
| 2013/0197357 A1* | 8/2013 | Green | A61B 5/743 600/424 |
| 2013/0288214 A1* | 10/2013 | Kesavadas | G09B 23/285 434/262 |
| 2013/0317352 A1* | 11/2013 | Case | A61B 8/0841 600/424 |
| 2013/0317363 A1 | 11/2013 | Case et al. | |
| 2014/0107731 A1* | 4/2014 | Stone | A61N 1/0529 607/59 |
| 2014/0228835 A1* | 8/2014 | Mielekamp | A61B 34/10 606/34 |
| 2014/0272866 A1* | 9/2014 | Kim | G09B 9/00 434/262 |
| 2015/0087975 A1* | 3/2015 | Salcudean | A61B 8/0858 600/438 |
| 2015/0088107 A1* | 3/2015 | Aljuri | A61B 1/307 606/10 |
| 2015/0356891 A1* | 12/2015 | Will | G09B 23/285 434/272 |
| 2016/0038247 A1* | 2/2016 | Bharadwaj | G06F 3/04847 600/426 |
| 2016/0147308 A1* | 5/2016 | Gelman | G06F 3/017 345/156 |
| 2017/0189721 A1* | 7/2017 | Sumanaweera | A61N 5/1049 |
| 2017/0209218 A1* | 7/2017 | Sahay | A61B 6/032 |
| 2018/0344390 A1* | 12/2018 | Brannan | A61B 18/1206 |

FOREIGN PATENT DOCUMENTS

| | | | |
|---|---|---|---|
| CN | 102429726 A | 5/2012 | |
| CN | 102647956 A | 8/2012 | |
| CN | 103417293 A | 12/2013 | |
| CN | 103417299 A | 12/2013 | |
| WO | 2007053676 A2 | 5/2007 | |
| WO | WO-2009139892 A1 * | 11/2009 | ........... G06F 19/325 |
| WO | WO-2015148378 A1 * | 10/2015 | ............. A61B 6/032 |

OTHER PUBLICATIONS

Office Action dated Jan. 4, 2016 in U.S. Appl. No. 12/275,699.
Acuity Lighting Group, "Visual Release 2.4 Professional Edition User's Guide", Aug. 15, 2006, http://www.visual-3d.com/support/documentation.aspx, pp. 1-181.
InnovMETRIC Software Inc., "PolyWorks® V10 Beginner's Guide", Feb. 2007, InnovMETRIC Software Inc., pp. 1-121.

(56) References Cited

OTHER PUBLICATIONS

European Search Report corresponding to European Serial No. 08852922.7 dated Nov. 23, 2012.
International Preliminary Report on Patentability dated May 11, 2017 in International Application PCT/US2015/058441.
Office Action dated May 15, 2018 in U.S. Appl. No. 12/275,699.
Notice of Allowance dated May 24, 2019 in U.S. Appl. No. 12/275,699.
Office Action dated Oct. 22, 2019 in Chinese Application 201580060066.2.
Office Action dated Jul. 16, 2020 in Chinese Application 201580060066.2.
Office Action dated Feb. 4, 2021 in Chinese Application 201580060066.2.

* cited by examiner

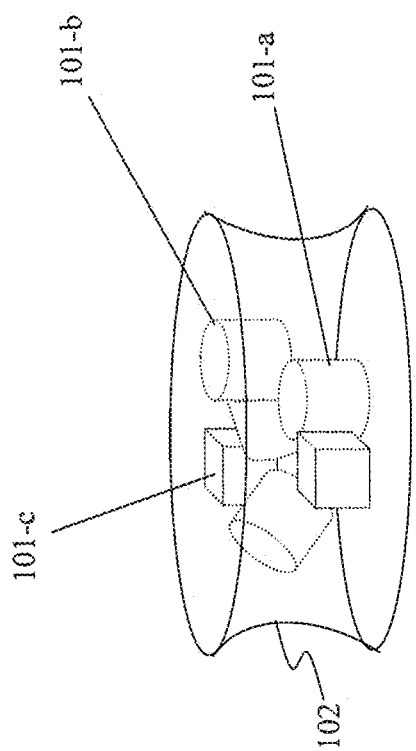

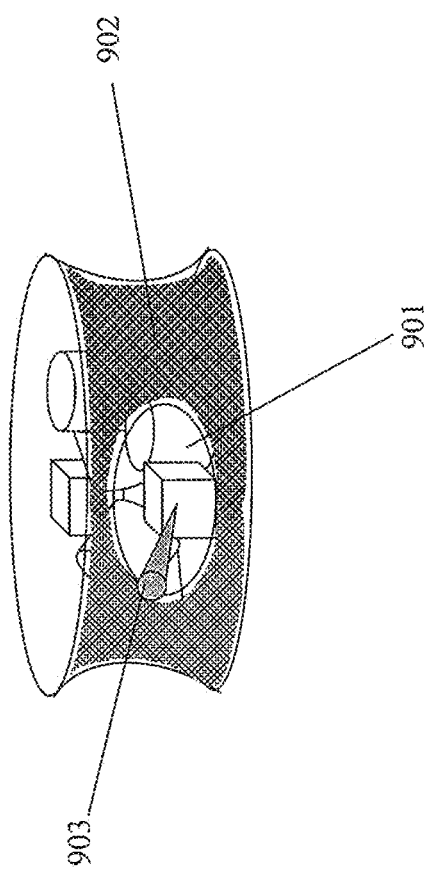

METHOD AND SYSTEM FOR ADJUSTING INTERACTIVE 3D TREATMENT ZONE FOR PERCUTANEOUS TREATMENT

CROSS-REFERENCE TO RELATED APPLICATIONS

The present application claims priority to U.S. Provisional Application Ser. No. 62/073,420, filed Oct. 31, 2014, entitled "Method and System for Adjusting Interactive 3D Treatment Zone for Percutaneous Thermal Ablation Surgery With Real Time Visual Feedback," which is incorporated herein by reference in its entirety.

The present application is a continuation-in-part of U.S. Non-Provisional application Ser. No. 12/275,699, filed Nov. 21, 2008, entitled "Method and System for Interactive Percutaneous Pre-operation Surgical Planning," which claims priority to U.S. Provisional Application Ser. No. 60/989,580, filed Nov. 21, 2007, entitled "Interactive Computer Graphic Tool for Percutaneous Surgical Procedure Planning," both of which are incorporated herein by reference in their entireties.

BACKGROUND

1. Technical Field

The present teaching relates to surgical procedure planning. More specifically, the present teaching is pertaining to interactive medical image processing for surgical procedure planning.

2. Discussion of Technical Background

With the advancements made in the field of medical imaging, minimally invasive techniques for the ablation of liver tumors have been made possible. Among such minimal invasive techniques, percutaneous thermal ablation has been studied in different forms. Currently, percutaneous radiofrequency ablation is one of the most promising alternatives to open surgery for the treatment of liver cancer. This operation is a minimally invasive procedure in which a needle (probe) is inserted into targeted tissues that are destroyed by heat. This modality has been introduced for treating patients who have non-resectable hepatic metastases. The success of such an operation depends largely on the accuracy of the needle insertion because when it is accurate, it is possible to destroy the whole tumor without damaging nearby organs so as to minimize the risks of a local recurrence. To ensure accuracy, a preoperative treatment planning is usually performed, which is one of the crucial factors in avoiding complications or even deaths.

Conventionally, a radiologist who performs a preoperative treatment planning relies on images of two dimensional (2D) scanned slices to determine the positioning of the needles. Unfortunately, this makes the planning of such a treatment rather difficult when relying only on 2D scanner slices. Most of existing systems or software display probes and treatment zones in a 2D slices with 2D overlay of affected region. Some existing systems can also display treatment zone in 3D and provide 3D pose adjustment. However, there is neither any existing system that can manipulate treatment zone size and shape directly in 3D, nor any existing system that can reflect real-time impact to the shape of treatment zone by other thermal dissipation structures in 3D.

Therefore, there is a need for a solution which can be used to assist a medical personnel to perform a preoperative treatment planning in a more reliable and accurate manner

SUMMARY

The present teaching relates to surgical procedure planning. More specifically, the present teaching is pertaining to interactive medical image processing for surgical procedure planning.

In one example, a method, implemented on a computing device having at least one processor, storage, and a communication platform capable of connecting to a network for surgical procedure planning is disclosed. At least one three dimensional (3D) object contained in a 3D volume is rendered on a display screen. The at least one 3D object includes a 3D object corresponding to an organ. First information related to a 3D pose of a surgical instrument positioned with respect to the at least one 3D object is received from a user. A 3D representation of the surgical instrument is rendered in the 3D volume based on the first information. Second information related to a setting of the surgical instrument is received from the user. A 3D treatment zone in the 3D volume with respect to the at least one 3D object is estimated based on the first and second information. The 3D treatment zone in the 3D volume is visualized on the display screen. The 3D representation of the surgical instrument and the 3D treatment zone are to be used for surgical procedure planning. One or more controls associated with the 3D representation of the surgical instrument and/or the 3D treatment zone are provided to facilitate the user to dynamically adjust the 3D treatment zone via the one or more controls.

In a different example, a system for surgical procedure planning is disclosed. The system includes a three dimensional (3D) scene rendering mechanism, a probe handling module, a control handling module, a treatment zone calculation module, and a treatment zone rendering mechanism. The 3D scene rendering mechanism is configured for rendering at least one 3D object contained in a 3D volume on a display screen. The at least one 3D object includes a 3D object corresponding to an organ. The probe handling module is configured for receiving, from a user, first information related to a 3D pose of a surgical instrument positioned with respect to the at least one 3D object. The probe rendering mechanism is configured for rendering a 3D representation of the surgical instrument in the 3D volume based on the first information. The control handling module is configured for receiving, from the user, second information related to a setting of the surgical instrument. The treatment zone calculation module is configured for estimating a 3D treatment zone in the 3D volume with respect to the at least one 3D object based on the first and second information. The treatment zone rendering mechanism is configured for visualizing the 3D treatment zone in the 3D volume on the display screen. The 3D representation of the surgical instrument and the 3D treatment zone are to be used for surgical procedure planning. The control handling module is further configured for providing one or more controls associated with the 3D representation of the surgical instrument and/or the 3D treatment zone to facilitate the user to dynamically adjust the 3D treatment zone via the one or more controls.

Other concepts relate to software for implementing the present teaching on surgical procedure planning. A software product, in accord with this concept, includes at least one non-transitory machine-readable medium and information carried by the medium. The information carried by the medium may be executable program code data, parameters in association with the executable program code, and/or information related to a user, a request, content, or information related to a social group, etc.

In one example, a non-transitory machine readable medium having information recorded thereon for surgical procedure planning is disclosed. The recorded information, when read by the machine, causes the machine to perform a series of processes. At least one three dimensional (3D) object contained in a 3D volume is rendered on a display screen. The at least one 3D object includes a 3D object corresponding to an organ. First information related to a 3D pose of a surgical instrument positioned with respect to the at least one 3D object is received from a user. A 3D representation of the surgical instrument is rendered in the 3D volume based on the first information. Second information related to a setting of the surgical instrument is received from the user. A 3D treatment zone in the 3D volume with respect to the at least one 3D object is estimated based on the first and second information. The 3D treatment zone in the 3D volume is visualized on the display screen. The 3D representation of the surgical instrument and the 3D treatment zone are to be used for surgical procedure planning One or more controls associated with the 3D representation of the surgical instrument and/or the 3D treatment zone are provided to facilitate the user to dynamically adjust the 3D treatment zone via the one or more controls.

Additional features will be set forth in part in the description which follows, and in part will become apparent to those skilled in the art upon examination of the following and the accompanying drawings or may be learned by production or operation of the examples. The features of the present teachings may be realized and attained by practice or use of various aspects of the methodologies, instrumentalities and combinations set forth in the detailed examples discussed below.

BRIEF DESCRIPTION OF THE DRAWINGS

The methods, systems, and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 1(a) depicts a three dimensional (3D) volume having 3D objects contained therein;

FIG. 9 presents an exemplary way to visualizing different zones for placing a probe, according to an embodiment of the present teaching;

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, systems, components, and/or circuitry have been described at a relatively high-level, without detail, in order to avoid unnecessarily obscuring aspects of the present teachings.

This present teaching is pertaining to interactive adjustment of a three dimensional (3D) treatment zone for percutaneous thermal ablation probe. It may be used in pre-surgical planning for percutaneous procedures such as radiofrequency ablation, microwave ablation, or cryoablation to help doctors better observe and decide the effective treatment area. It can provide unique interaction schemes such as on-probe controls or on-zone controls for treatment zone adjustment in 3D. It may also provide a more intuitive and real-time feedback of the impact to the zone by surrounding thermal dissipation structures.

Figure 1B:
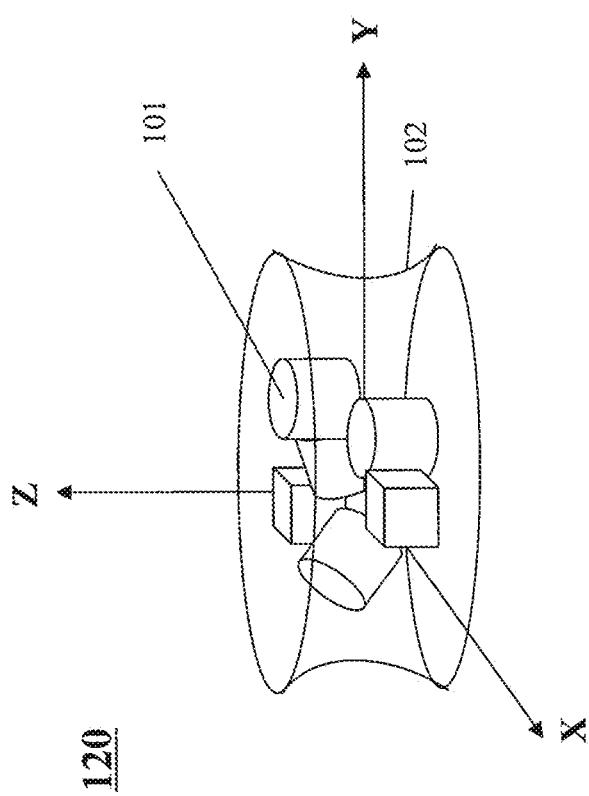
FIG. 1(b) shows a 3D volume containing 3D objects displayed in a 3D coordinate system.

FIG. 1(a) depicts a three dimensional scene with a 3D volume 100 having three dimensional objects rendered therein. As shown, the 3D volume 100 has been segmented into several objects 101-a, 101-b, . . . , 101-c, and 102. These objects may correspond liver, lesions, bones, arteries, vital organs, or skin (e.g., 102). Each 3D object may correspond to a sub 3D volume within the 3D volume 100. The 3D volume 100 may be visualized on a 2D display screen such as a computer display screen. Such visualization may be performed in a well-defined 3D coordinate system. This is shown in FIG. 1(b), in which the 3D volume 100 is displayed in a 3D space defined by a coordinate system 120 with three axes, X, Y, and Z. The 3D volume 100 may be rendered on a 2D display screen with respect to the 3D coordinate system 120 with a particular 3D pose, including its geometric position and orientation.

In some embodiment, the 3D volume 100 may be sliced into a plurality of 2D slices along some 3D orientation so that each of the slices provides 2D imagery of the 3D volume 100 along a certain direction. To facilitate effective 3D visualization, these 2D slices can be placed inside this 3D scene to enable a viewer to observe the composition of different objects, if any, on a planar surface. Through this means, one may be able to observe the spatial relationship among different segmented 3D objects. The concept is described in U.S. Pat. No. 7,315,304, entitled "Multiple Volume Exploration System and Method".

Figure 1C:
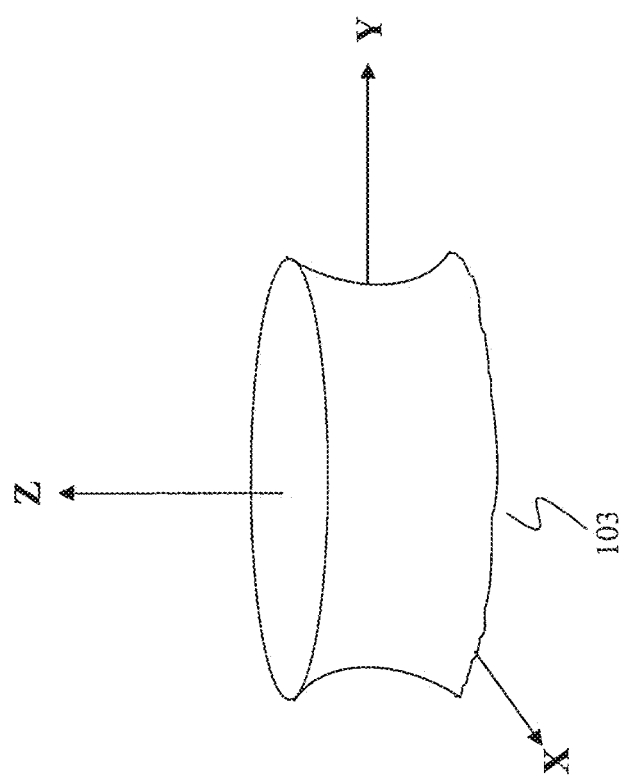
FIG. 1(c) shows a 3D volume displayed in a 3D coordinate system in an opaque mode.

A user may manipulate the visualization of the 3D volume 100 in different ways. For example, the entire 3D volume may be rotated and translated with respect to the 3D coordinate system 120. This may facilitate the user to observe the spatial relationships among different objects from different angles. In addition, the visualization of each segmented object can be independently manipulated, e.g., a 3D object may be made visible or invisible so that a user can see the areas of the 3D volume 100 where it is occluded by the selected 3D object. This may be done by adjusting the transparency of such selected 3D object. When the selected 3D object is made completely transparent or highly translucent, an object occluded by the selected 3D object can be made more visible. In some embodiments, a 3D object of interest can be made opaque and when additional 2D slices for that object are also rendered, one can be more clearly observe the internal structure of the 3D object. For example, when a 3D object corresponds to skin of a human body, when a user elects to visualize the skin in a transparent mode, all the objects inside of the skin structure can be made visible. On the other hand, if the user elects to visualize the skin in an opaque mode, none of the 3D objects wrapped inside of the skin will be visible. This is shown in FIG. 1(c), where the skin object 102 is visualized in an opaque mode 103 and none of the objects inside of the skin is visible. In some embodiments, the level of transparency may be adjusted gradually and interactively to meet a user's needs.

Figure 2A:
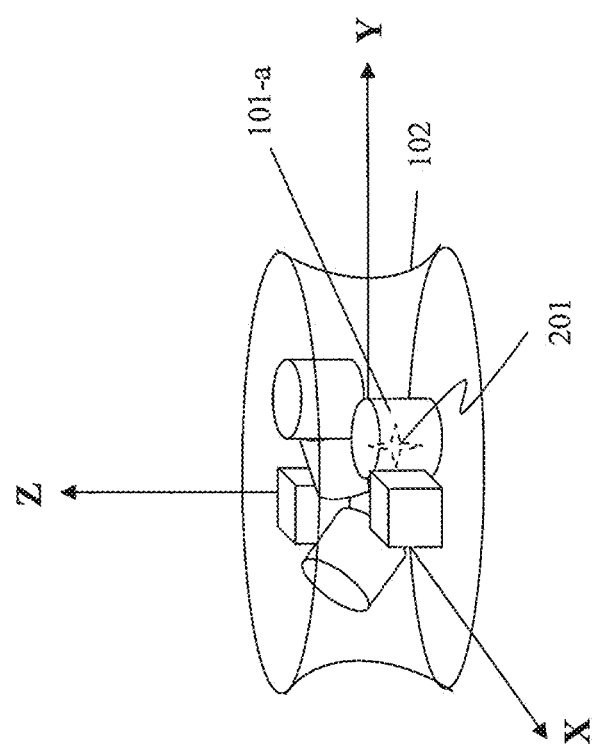
FIG. 2(a) depicts a 3D scene having 3D objects displayed therein and 3D point specified in the 3D scene for placing a virtual probe, according to an embodiment of the present teaching.

FIG. 2(a) depicts a three dimensional scene 300 having three dimensional objects displayed therein and a 3D location specified, according to an embodiment of the present teaching. To perform a percutaneous pre-operational surgical planning, a user may interactively interface with a system developed in accordance with the present teaching to specify a 3D location at which a virtual probe is to be placed. This is shown in FIG. 2(a) where a 3D location 201 is determined in accordance with a 2D position specified on a, e.g., display screen. Such a specification may be done via various known techniques such as a mouse click on a display screen. A screen point determined via, e.g., a mouse click, may correspond to a 2D coordinate with respect to a 2D coordinate system defined based on the underlying display screen. Such a 2D coordinate needs to be transformed into a 3D coordinate point in the 3D scene 300, which can be done by translating the 2D coordinate into a 3D coordinate via a transformation. Such a 2D coordinate may be selected with respect to a 3D object (e.g., skin 102) in the 3D scene and the 3D location transformed may correspond to a 3D location on the 3D object at which a virtual probe or needle is to be virtually placed in order to simulate the effect of percutaneous surgery in a percutaneous pre-operational surgical planning procedure.

Figure 2B:
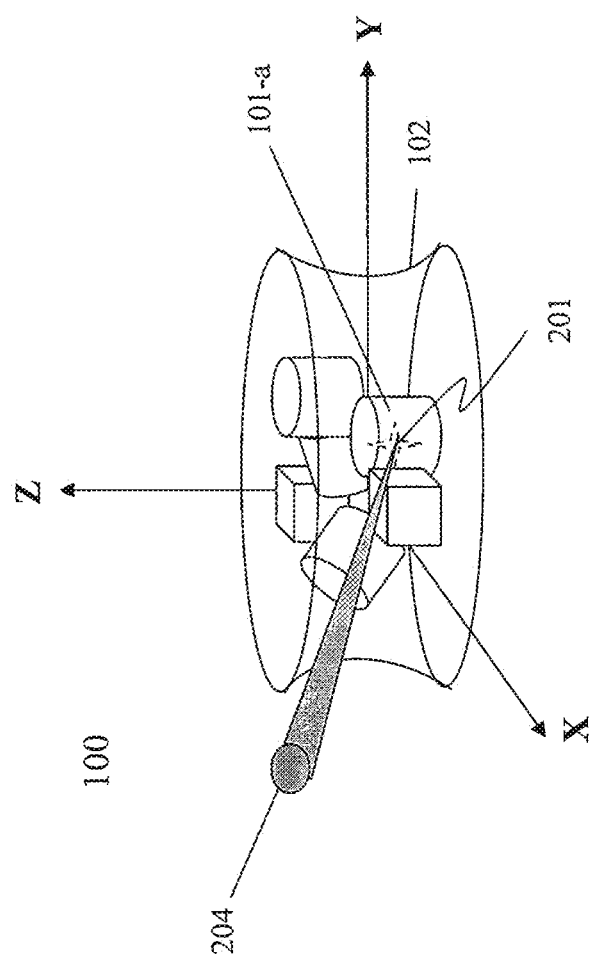
FIG. 2(b) depicts a 3D scene with a plurality of 3D objects displayed therein and a movable and adjustable probe being placed at a specified 3D point near an object, according to an embodiment of the present teaching.
Figure 3:
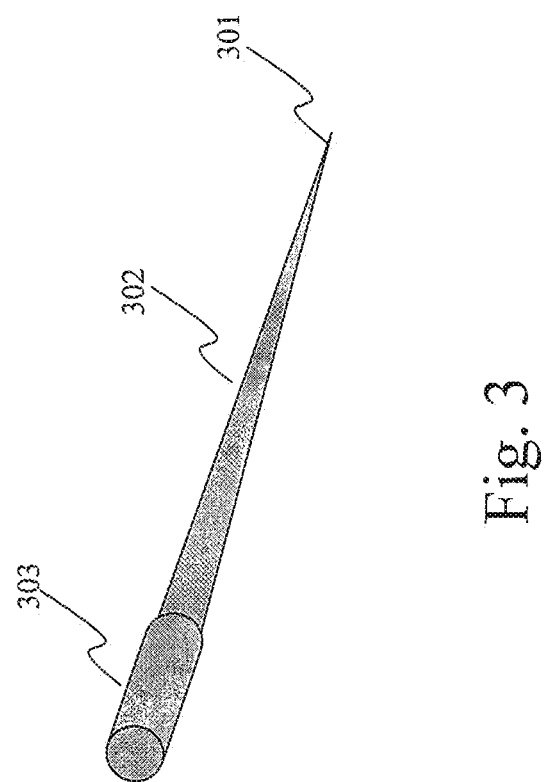
FIG. 3 shows an exemplary structure of a movable and adjustable probe, according to an embodiment of the present teaching.

FIG. 2(b) shows that once the 3D coordinate corresponding to a 2D point selected on a display screen is determined, a virtual probe or needle 204 may be virtually placed at the 3D coordinate position in the 3D space 300. The virtual probe or needle 204 may have a straight shape or any other shape as needed, as shown in FIG. 3. In some embodiments, a virtual probe may be constructed to have a tip 301, a body 302, and a handle 303. The tip 301 is where the virtual probe 204 is placed on a 3D object (e.g., object 102 in FIG. 2(b)). Through appropriate interfaces and tools (see description below with reference to FIG. 8), a user may manipulate the movement of the virtual probe 204 via certain part of the probe, e.g., the body 302 or handle 303. For example, in a percutaneous pre-operational surgical planning for liver disease, a lesion may be selected as a 3D object to which a virtual probe is to be placed (e.g., object 101-a) and the point at which the virtual probe and the human skin intersect is where a needle in real operation may need to be placed.

The virtual probe, once inserted, may be adjusted. This may be done by allowing a user to use a tool (e.g., in a GUI, use a drag and pull motion) to move different parts of the virtual probe based on needs. For example, a user may be allowed to drag the tip 301 of the probe and pull to a desired 3D location. A user may also be allowed to grab the body 302 of the probe and drag it so that the tip of the probe remains the same. Similarly, a user may be allowed to drag the handle 303 of the tip and move around. In other embodiments, a user may be allowed to move the tip by dragging the body 302 or the handle 303.

Figure 4A:
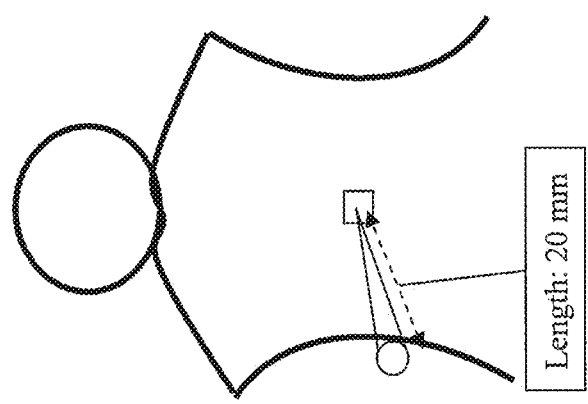
FIGS. 4(a)-4(c) show different variations associated with movable and adjustable features of a virtual probe, according to an embodiments of the present teaching.

When a virtual probe is created, it may have a certain length and such a length may be displayed along with the probe (see FIG. 4(a)). The probe length can be dynamic or fixed. A fixed-length probe may be used to mimic the commercial needle electrode systems which commonly have length of 10 cm, 15 cm, and 20 cm. Different lengths may be made available and a user may select any one of the available lengths.

Figure 4C:
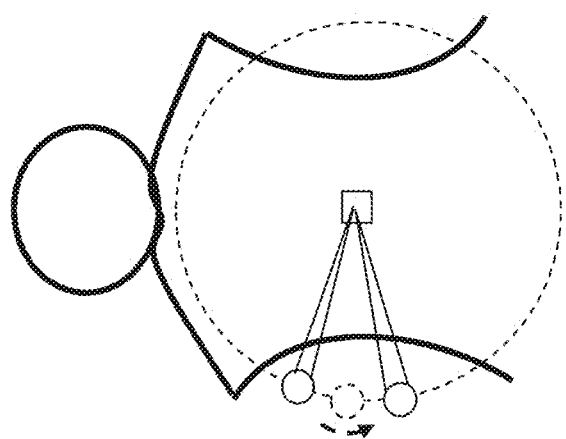

A configuration using a probe of a fixed length may be helpful in terms of having a more realistic simulation in pre-surgical planning. When a probe is configured with a fixed length, the movement of the probe may be accordingly determined. For instance, e.g., the movement of the probe may be confined to skin 102, or to a half sphere with respect to the tip of the probe when the length of the probe is fixed. This is shown in FIG. 4(c). However, when a user selects a different length for the probe, the scope of allowed movement of a probe may be accordingly or automatically adjusted.

Figure 4B:
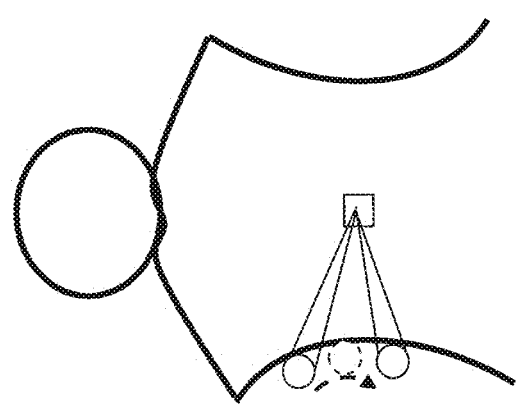

In some embodiments, the length of a probe may be made dynamic. A user can use a probe with a dynamic length as shown in FIG. 4(b). The scope of movement of a probe with a dynamic length may be defined with respect to the tip of the probe. In this case, the movement of the probe may be constrained on, e.g., a skin surface. The probe's angles with respect to a coordinate system, such as patient coordinate system, may be displayed on the screen in real-time while the probe is being manipulated.

Figure 5:
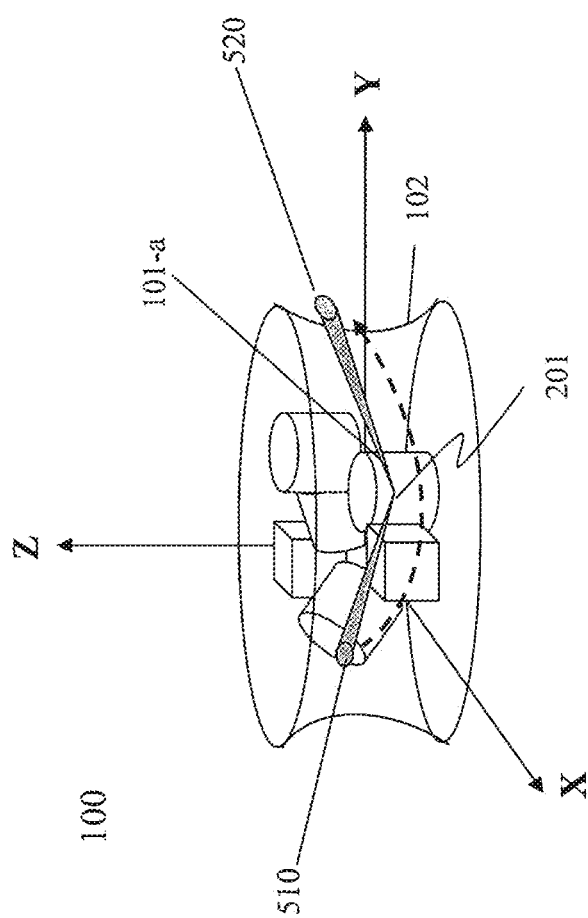
FIG. 5 illustrates multiple probes placed in a 3D volume, according to an embodiment of the present teaching.

In some embodiments, more than one probe may be placed. FIG. 5 illustrates two probes 510 and 520 being placed on the same 3D location of a selected object. This may be helpful to provide a user the ability to experiment with more than one probe simultaneously and make it possible to assess the possibility of utilizing multiple probes in the same treatment and effect thereof.

Figure 6:
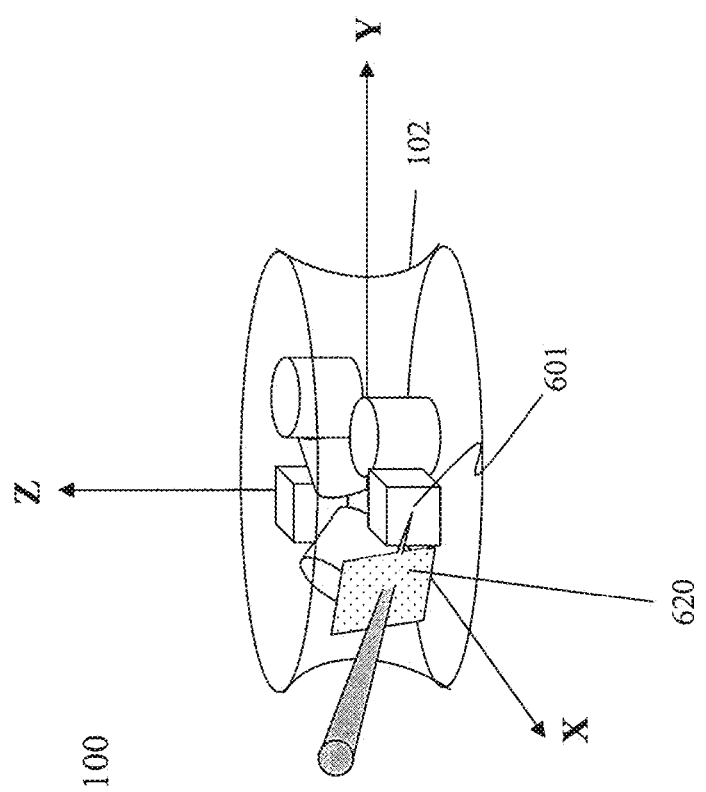
FIG. 6 depicts a probe placed near a 3D object with a 2D cross sectional view of the 3D object at a certain location of the probe to show the anatomical structure near the probe, according to an embodiment of the present teaching.
Figure 7:
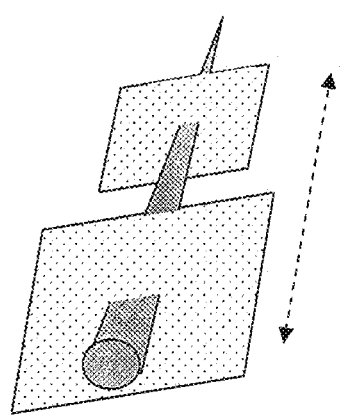
FIG. 7 illustrates the scenario in which a user can dynamically adjust the viewing of anatomical structure by sliding the cross sectional view along a probe, according to an embodiment of the present teaching.

The system according to the present teaching may also provide the means to allow a user to view the anatomical structure of a 3D object along a probe that has been placed. In FIG. 6, an orthogonal probe view 620 is provided that corresponds to a 2D slice image of the 3D object 601. This 2D slice image may be a view centered at the probe and orthogonal to the probe. Through this view, a user can see what structures are passed through by the probe in a two-dimensional image view. A user may also be allowed to move the viewing plane up and down along the probe by dragging along the probe body, as illustrated in FIG. 7. User can also activate an automatic movement function so that the probe view may automatically move up and down along the probe according to a particular time interval.

FIG. 8 illustrates the concept of detecting an obstacle encountered by a probe, according to an embodiment of the present teaching. In some medical applications, an actual or physical probe cannot go through some parts of the body such as bones, vital organs, or major arteries. Such parts of the body may be categorically defined as obstacles or prohibited parts. According to the present teaching, mechanisms and method are provided to automatically detect collision when a probe intersects with such parts of the body. A system in accordance with the present teaching may define default obstacles or prohibited parts. In some embodiment, it can also provide flexible means for a user to dynamically define such obstacles according to the needs of specific applications. For instance, in some applications, bones may be an obstacle. However, in other applications, bones may be a target area for which a probe needs to be placed.

Figure 8A:
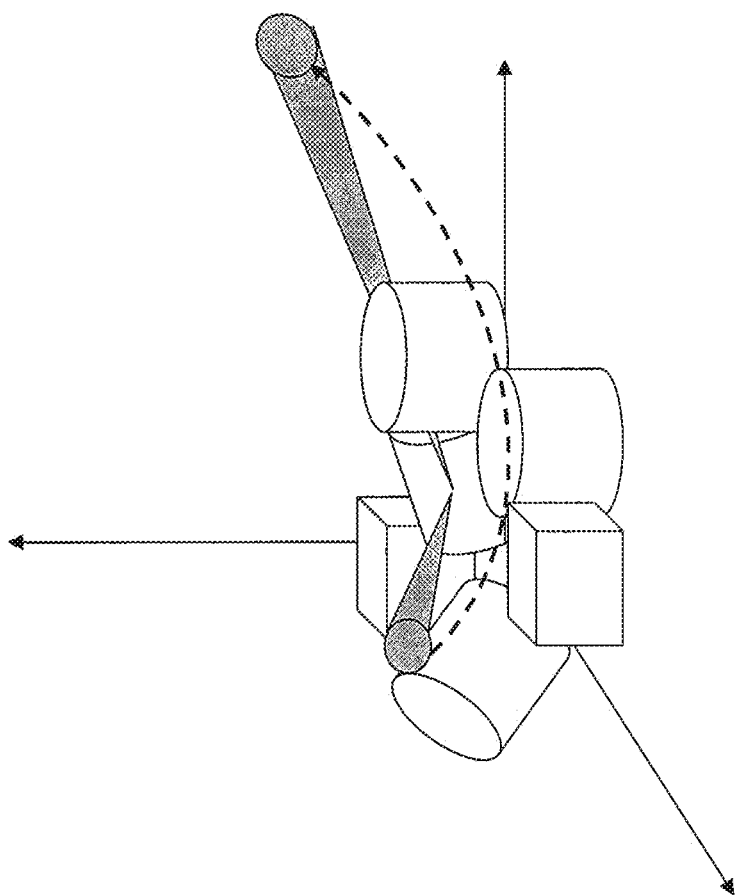
FIG. 8(a) illustrates the concept of detecting an obstacle encountered by a probe, according to an embodiment of the present teaching.
Figure 8B:
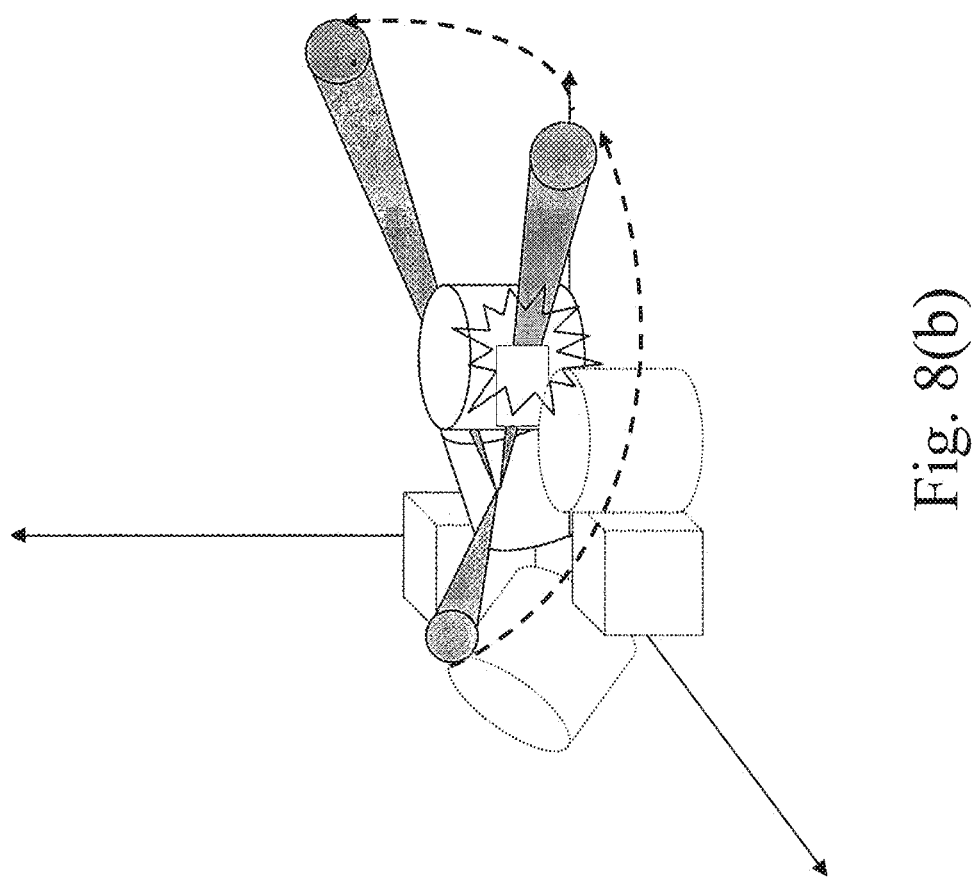
FIG. 8(b) depicts an exemplary means to generate a warning of a detected obstacle, according to an embodiment of the present teaching.

When obstacles are defined, the system may provide automatic collision detection capabilities while a probe is placed into a 3D scene. In FIG. 8(a), it is shown that whenever a probe is placed, collision detection may be applied automatically. When a user moves a probe around, whenever the probe hits any of the defined obstacles, the system may alert the user. Example ways to alert a user is to create an alarming visual effect such as using a visually stimulating color or generate an audio sound. This is illustrated in FIG. 8(b). Such a feedback is to generate a warning effect to catch the user's attention. For different obstacles, different colors or sounds may be used so that the user can recognize the type of obstacle associated with each different warning. Audio feedback may also be design to indicate orally the type of obstacle encountered.

In some embodiments, obstacles may be individually turned on or off so that a user can experiment and explore different scenarios when moving and inserting the probe.

Once obstacles or areas where a probe is prohibited to enter, it may also be possible to mark up such regions in the 3D scene as areas that the probe may not enter. For example, in some procedures, bones may be considered as obstacles. In addition, major arteries may likely be considered as areas that are constrained or prohibited regions. According to the present teaching, means may be provided to automatically identify these constrained regions and mark as such on the skin surface corresponding to such prohibited areas. This is illustrated in FIG. 9, in which the skin surface is marked as two zones. One corresponds to an area 901 where a probe 903 can enter and the other area 902 is an area where the probe 903 is not allowed. Such zones are computed with respect to a specific target position, which corresponds to a target object inside the skin where the treatment is to be delivered through an actual needle. Therefore, Zone 901 is a valid insertion zone which is the area that the probe 903 can reach a target position of the target object without encountering any obstacles or constraints. The other zone 902 is an area that the probe is obstructed by some obstacles or constraints. Different zones may be displayed using a different visual effect such as using different colors or with different appearance such as transparency.

Figure 10:
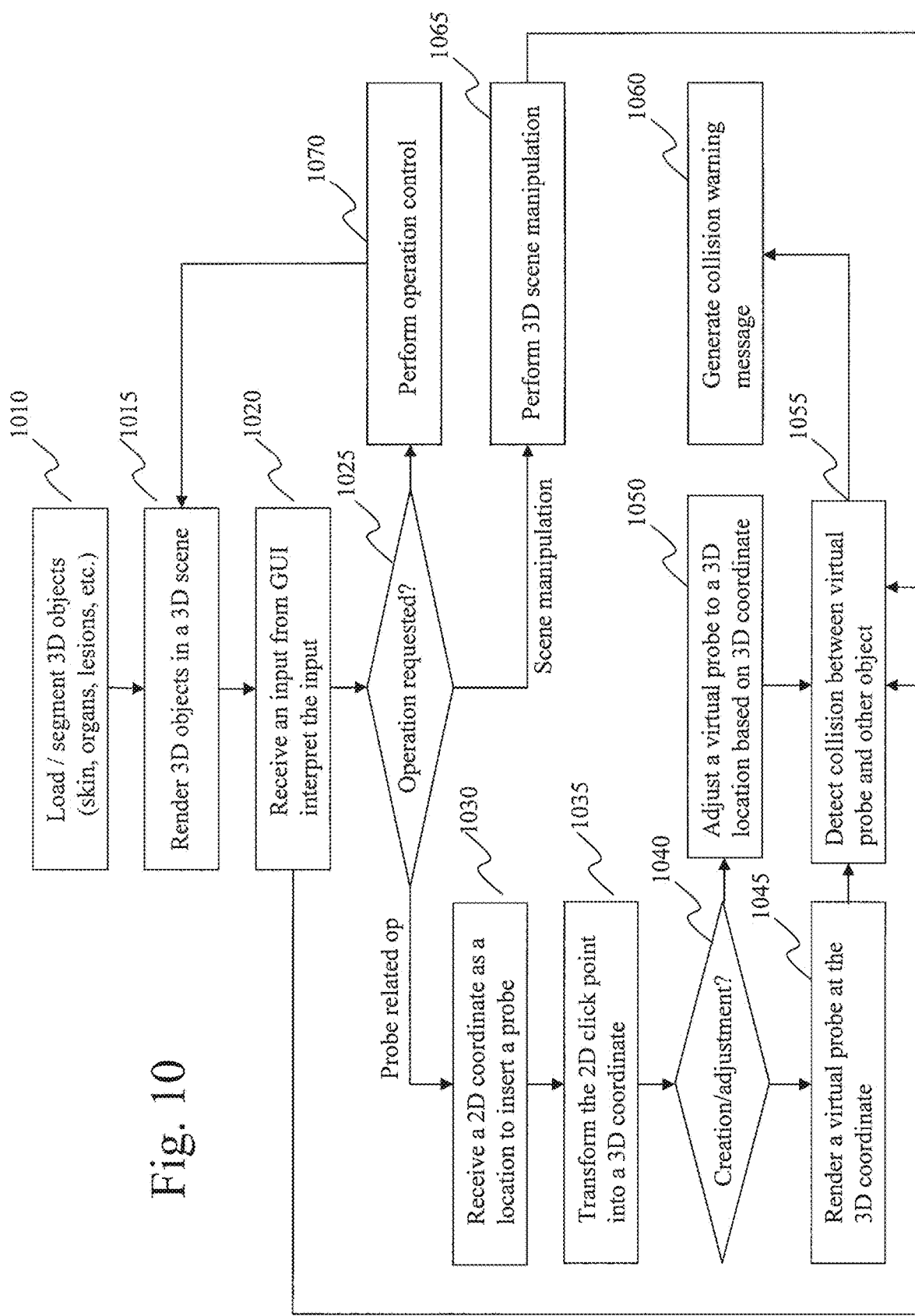
FIG. 10 is a flowchart of an exemplary process, in which a virtual probe is placed, manipulated, and rendered based on optional conditions specified by a user, according to an embodiment of the present teaching.

FIG. 10 is a high level flow of an exemplary process, in which a percutaneous pre-surgical planning process is carried out, according to an embodiment of the present teaching. Volumetric data may be first loaded into a system at 1010. In some embodiments, such loaded volumetric data may be further processed, at 1010, to extract different segmented 3D objects. In some embodiment, the loaded data may have been previously segmented and one or more 3D objects may already exist. Once loaded, the 3D volume and the 3D objects contained therein are rendered in a 3D scene at 1015. After the 3D volume and the 3D objects are displayed on a display screen, a user may enter an instruction to interact with the system during a percutaneous pre-surgical planning process. A user input may be issued via different means. For instance, an input may be related to an action such as a mouse click on some control buttons or a selection of a plurality of available choices.

Such a user input may be dispatched to relative action modules according to the nature of the input or some preset system configurations. When the system receives an input, the input is interpreted at 1020. There may be different types of input. One exemplary type of input relates to definitions such as definitions of a target object, an obstacle, or a prohibited region in a 3D volume. Another exemplary type of input is an instruction related to insertion, manipulation, and visualization of different 3D objects in the process of a percutaneous pre-surgical planning.

Regarding defining different types of objects, depending on the nature of a particular procedure, a different target object may be defined. For instance, for a procedure to treat liver tumor, a lesion in a liver may identified as a target object. For each procedure, different types of obstacle may also be defined. An obstacle may be defined to be an object that a probe cannot penetrate. One example of such an obstacle may be bones. However, if a different procedure requires a probe to enter into a bone structure, bones may be defined as target rather than obstacle. Another exemplary type of object is a prohibited region, which may be defined as a region that if a probe's entry may cause harm. For instance, a user may select one or more major arteries around a liver as prohibited regions to enter a probe. In this example, to allow a probe to enter into a lesion inside a liver, the probe has to take a route that avoids the bones and major arteries.

Selections of target object, obstacles, or prohibited regions may be made based on a plurality of choices, which may correspond to all the segmented 3D objects. For instance, the segmented objects in a 3D volume representing a human body may include skin, liver, pancreas, kidney, lesions inside or nearby certain organs, surrounding tissue, bones, blood vessels, etc. Depending on the procedure to be performed, a lesion associated with, e.g., the liver may be selected as a target object. Depending on the specific treatment to be performed, different obstacles or prohibited regions may be selected. For instance, for percutaneous treatment, bones may be selected as obstacles and major blood vessels may be selected as prohibited regions. Once such selections are interpreted, the system sends such definitions to a collision detection operation at 1055, which utilizes such information in automatically detecting when a probe encounters or enters into such objects.

As discussed, another type of input corresponds to instructions related to insertion, manipulation, and visualization of different 3D objects. Different types of instructions may be further recognized. If the input instruction relates to insertion of a virtual probe, determined at 1025, the system further receives, at 1030, a 2D coordinate corresponding to a screen location specified by a user as where a probe is to reach. To translate the 2D screen location to a 3D coordinate at which a probe is to reach, a transformation between the 2D coordinate and a 3D coordinate is performed at 1035. Since a received 2D coordinate may correspond to either a user's desire to insert a new probe or to make an adjustment to an already inserted probe, it is further determined, at 1040, whether the operation requested corresponds to creation of new probe or adjusting an existing probe.

If the user's request is to insert a new probe, the system renders, at 1045, a new probe at the transformed 3D coordinate. The process then proceeds to detecting, at 1055, a potential collision between the probe and any other object that has been defined as either an obstacle or a prohibited region. If the user's request is to make an adjustment to an existing probe, the system adjusts, at 1050, the existing probe to the transformed 3D coordinate and then proceeds to collision detection at 1055. When a collision is detected, the system may generate a warning message, at 1060, to caution the user that the probe may have encountered some obstacle or entered into a prohibited region. The manner the warning message is generated and presented may depend on the system setting. For example, the system may be defaulted to flash on the location where the collision is detected (see FIG. 8(*b*)).

When there are multiple existing probes, an additional step (not shown) may be performed, in which the user and the system may interactively determine which probe is to be adjusted. In addition, the 2D coordinate received from the user may correspond to a manipulation with respect to the tip, the body, or the handle of a probe, depending on, e.g., what is the closest part and which mode of operation the system is placed under (not shown). For example, if the system is set in a mode in which a probe is to be manipulated using the handle of the probe, then the 3D coordinate transformed from the 2D coordinate received from the user is where the handle of the probe is to be re-located. If the probe is selected to have a fixed length, then the 3D coordinate needs also to be determined based on the fact that the handle of the probe has to be on a sphere centered around the tip of the probe. A user can also switch between different modes of operation. For instance, a user may elect first to adjust the probe's tip to a best location by manipulating with respect to the tip of the probe. Once the tip location satisfies the needs of a procedure, the user may then switch to a mode in which the manipulation of the probe is through the handle of the probe. Through such manipulation via the handle of the probe, the user may adjust the entry point of the probe on the skin, without affecting the tip position, to avoid any obstacle or prohibited regions.

If the input instruction relates to 3D scene manipulation, determined at 1025, the system proceeds to 1065 to handle 3D scene manipulation. 3D scene manipulation may include object oriented scene rotation, zooming, visualization mode, etc. In some embodiments, when a 3D scene is moved around, a probe that has been inserted into the 3D scene may be moved around accordingly. In this way, a user may be able to observe the spatial relationship between the probe and surrounding objects from different angles. In some embodiments, through 3D manipulation, a user may manipulate the visibility of individual object by, e.g., making them transparent, opaque, or translucent. In some situation, a user may also control to view a 2D cross sectional view of an object along the probe and may arbitrarily change the location at which a 2D cross sectional view is generated and displayed. In other embodiment, a user may also be able to manipulate the 3D scene via the probe by, e.g., dragging the handle of the probe to rotate the entire 3D scene.

In some embodiments, it can also set that manipulation to a 3D scene does not affect the 3D pose of the probe. This may be useful at times because the user can adjust the 3D volume, e.g., so that or until a collision is avoided. In this case, whenever the 3D scene is changed (e.g., rotated or translated), the system automatically proceeds to 1055 to detect collisions and subsequently report a collision at 1060 if it is detected.

Figure 11:
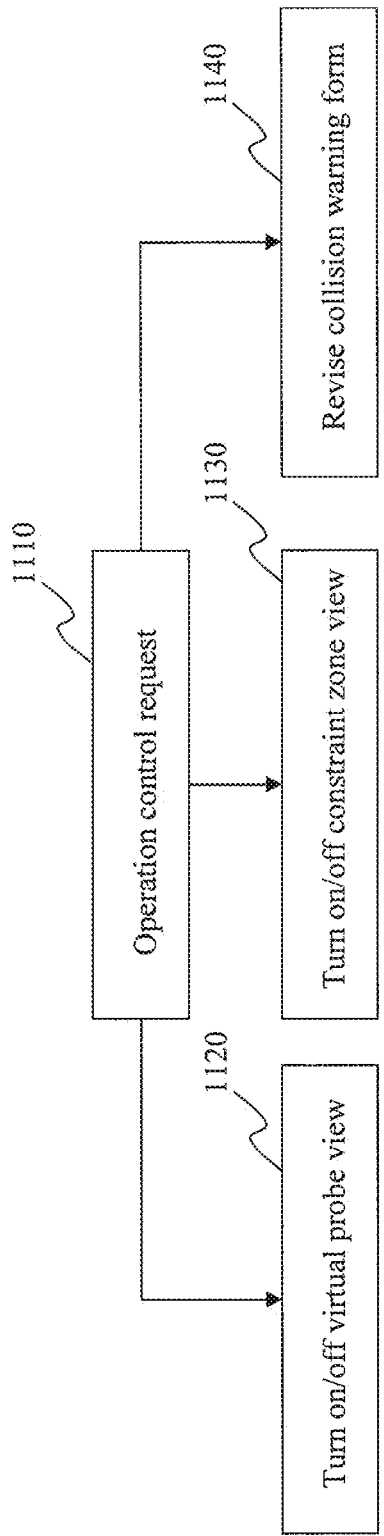
FIG. 11 illustrates exemplary types of operational control in percutaneous pre-surgical planning, according to an embodiment of the present teaching.

If the input instruction relates to operational control, determined at 1025, the system proceeds to 1070 to perform instructed control. There may be different types of operational controls. FIG. 11 illustrates some exemplary types. For instance, a user may control to turn on or off of the view of the virtual probe (1120). A user may also control to turn on or off the view in which different zones associated with certain constraint may be visually distinct (1130). A user may also control how a collision situation may be presented, e.g., visually or acoustically. In addition, as discussed earlier, a user may also control how to display a 3D object, e.g., opaque or transparent. This includes to control the display of each individual object or the entire 3D scene.

Figure 12:
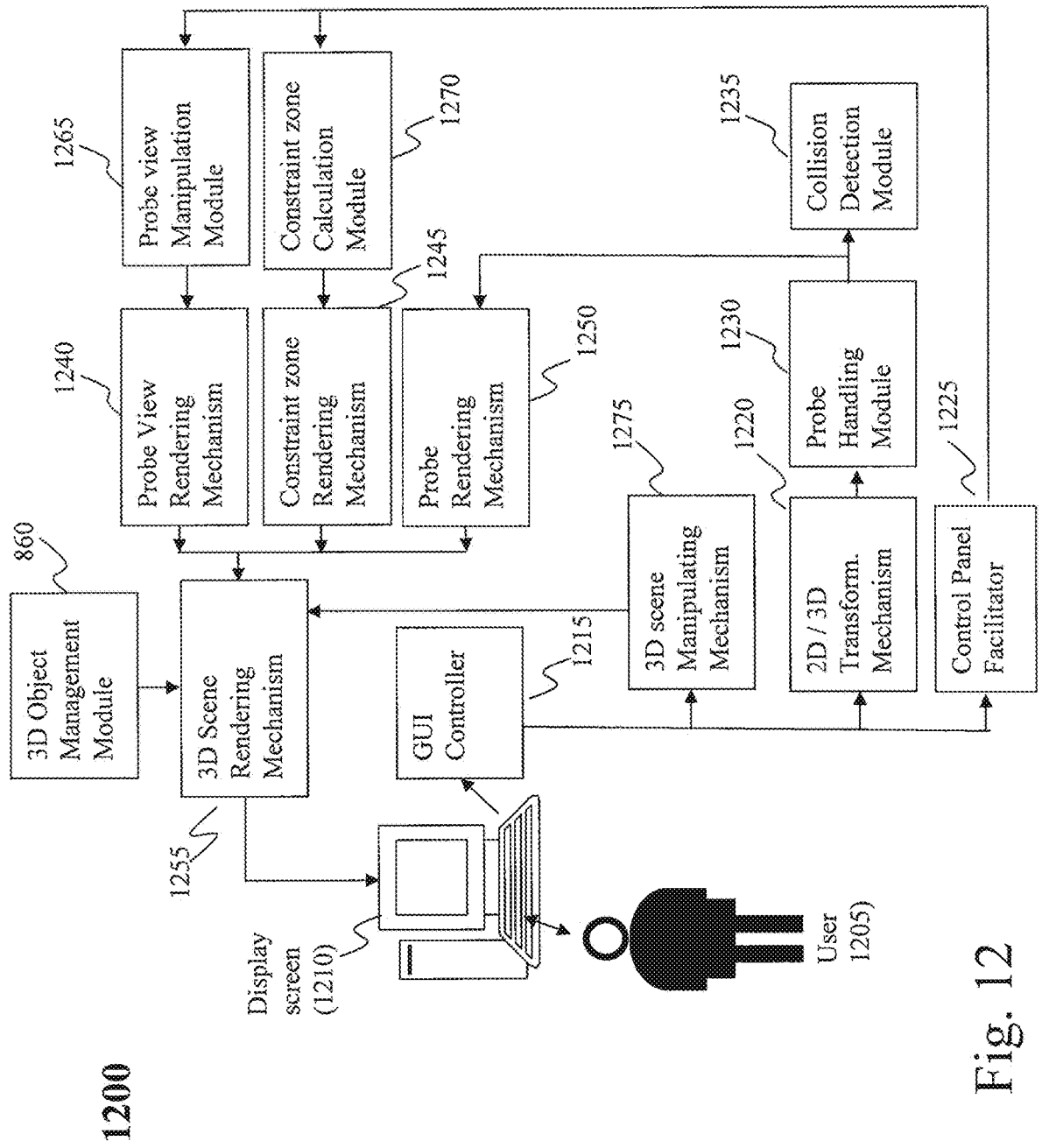
FIG. 12 depicts an exemplary construct of a system that facilitates 3D placement and manipulation of a virtual probe in a 3D environment, according to an embodiment of the present teaching.

FIG. 12 depicts a construct of an exemplary system 1200 that facilitates the placement and manipulation of a virtual probe in a 3D environment for percutaneous pre-operational surgical planning, according to an embodiment of the current invention. The system 1200 comprises a display device 1210, a graphical user interface 1215, a 2D/3D transformation mechanism 1220, a control panel facilitator 1225, a probe handling module 1230, a collision detection module 1235, a plurality of rendering mechanisms, including a probe view rendering mechanism 1240, a constraint zone rendering mechanism 1245, a probe rendering mechanism 1250, and a 3D scene rendering mechanism 1255, a 3D object management module 1260, a probe view manipulation module 1265, a constraint zone calculation module 1270, and a 3D scene manipulating mechanism 1275.

A user 1205 may interact with the system 1200 via a user interface displayed on the display device 1210. The GUI controller 1215 may control interaction between the system 1200 and user 1205. If the user 1205 desires to use a tool associated with a virtual probe once a 3D scene is set up, the user may request the system to retrieve 3D object information from the 3D object management 1260 and render such objects via the 3D scene rendering mechanism 1255. When such user request is entered via the user interface, the GUI controller 1215 may then interpret the request and accordingly activates appropriate functional modules to perform the requested operations.

For example, if request is to change the orientation of the 3D scene, the system may activate the 3D scene manipulator module 1275 to modify the orientation of the 3D scene based on the specification from the user. During this process, the user and the GUI controller may continuously interact, e.g., user may click a point in the 3D scene and drag along a certain direction so that the entire 3D scene may move along in the same direction. Similarly, the user may exercise the same control with respect to a particular 3D object such as a virtual probe.

A user may also interact with the system to exercise various controls over a probe. When the user manually controls a probe via a 2D display screen, the 2D/3D transformation mechanism 1220 dynamically transforms a 2D screen point to a 3D point in the 3D scene, and then pass the 3D point to the probe handling module 1230 which determines whether it is a new probe creation operation or an adjustment operation to be made to an existing probe. The desired probe is then rendered in the 3D scene by the probe rendering mechanism 1250. In the process of moving an existing probe, the collision detection module 1235 is operative to detect intersection between the applicable probe and any 3D objects that have been defined as either an obstacle or prohibited regions. The collision detection module 1235 may also generate warning information when a collision is detected.

As discussed herein, the system also provides the means for a user to exercise various control regarding the operation of the system. For example, via the control panel facilitator 1225, a user may activate or deactivate a probe view controlled by the probe view manipulation module 1265. A user may also control other visualization parameters such as transparency through the probe view rendering mechanism 1240. A user may also set desired mode of display which may also be personalized and such a setting may be applied automatically when the user signs up with the system. For example, a user may desire to always have the skin (a 3D object) displayed in a transparent mode. Another user may desire to have a particular sound as a warning whenever a collision is detected. A user may also control the activation or deactivation of computation of a constraint zone by interacting with the constraint zone calculation module 1270 or control the display of a detected constraint zone by interacting with the constraint zone rendering mechanism 1245.

Minimally invasive techniques for the ablation are becoming popular with advances in medical imaging. Among them, percutaneous thermal ablation has been studied in different forms such as radiofrequency ablation, microwave ablation, or cryoablation. This operation is a minimally invasive procedure that includes inserting a needle in targeted tissues and then destroys it using different levels of thermal energy. The success of such an operation mainly depends on the accuracy of the needle insertion, making it possible to destroy the whole targeted tumor, while avoiding damages on other organs and minimizing risks of a local recurrence. Therefore, the effective treatment zone planning is one of the crucial factors in determining the success or failure of the procedure.

As described above in the Background section, in order to obtain a more precise shape of the treatment zone, it is desirable to show it in a 3D environment. And it is more intuitive for human being because we perceive naturally in 3D. Moreover, when users concentrate on 3D looking at the relationships between the treatment zones and surrounding anatomic structures, it is better if they can adjust the size, shape, and pose of the treatment zone directly in 3D. Because users may lose focus if they have to move the gaze between the 3D space and a control widget for adjusting the zone in other places.

To provide this kind of direct manipulation, a system and method according to one embodiment of the present teaching enhance a 3D virtual probe with several on-probe controls. The end handle of the virtual probe may be used as pose manipulator to change the orientation and location of the probe. The body of the probe may have several control-handlers for adjusting settings of the probe, such as the model, the length, and the level of thermal energy of the probe. On-zone controls may be provided on the thermal treatment zone itself (e.g., placed on the border or edge of the 3D treatment zone) for adjusting the length, radius-width, and pre-gap size of the treatment zone. When users move the mouse to one of the on-zone locations of the treatment zone, they can activate a corresponding on-zone control such as for resizing the zone. The virtual probe may also show scales on the body of the probe so that users can see what the length of a probe should be used to approach the target from the entry point. Moreover, when a treatment zone is adjusted to touch or close to certain anatomic structures, a thermal dissipation model can be used to calculate the corresponding impact or changes to the shape of the zone. The affected zone may then be updated and visualized accordingly in real time.

Figure 13:
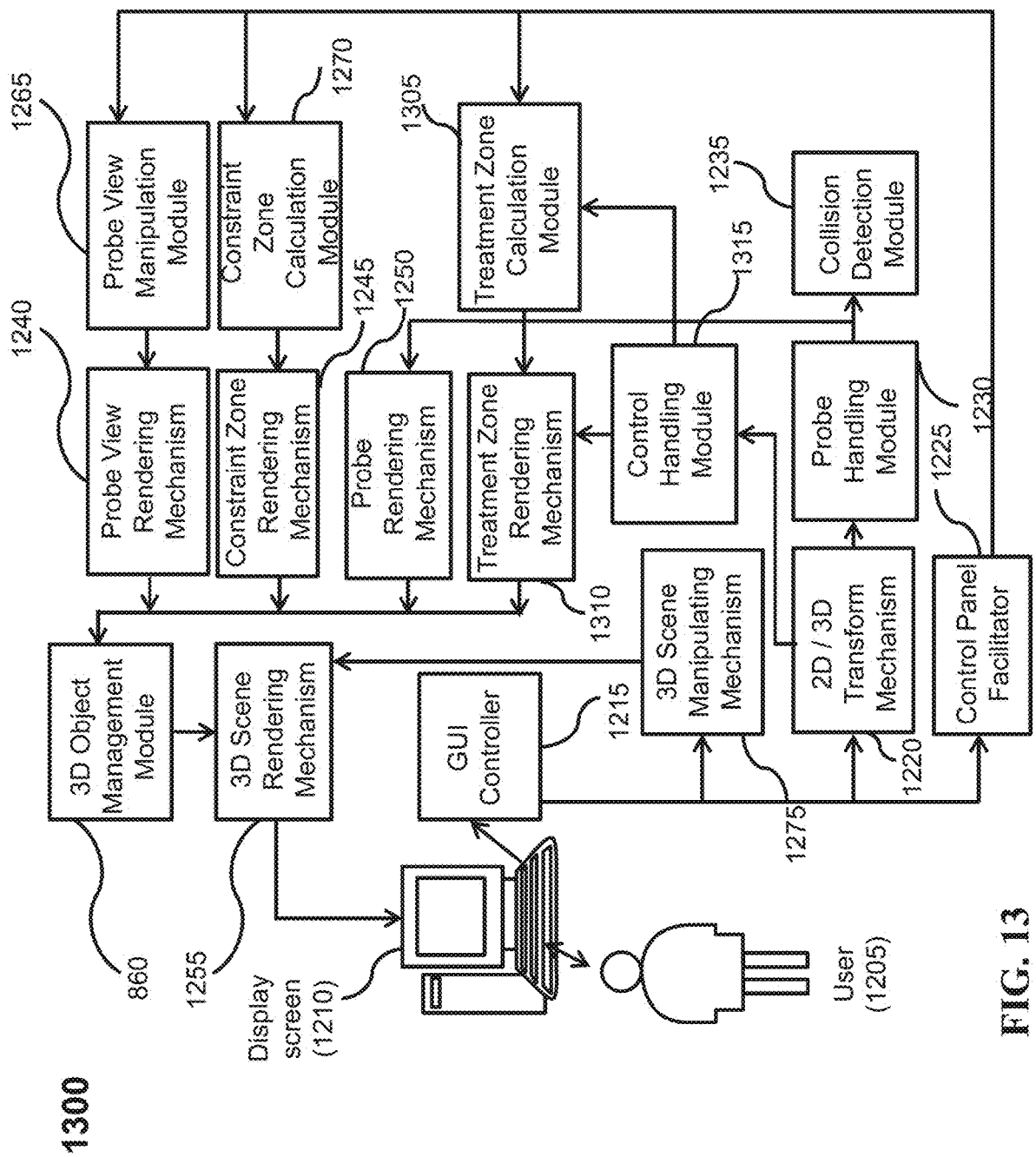
FIG. 13 depicts another exemplary construct of a system that facilitates 3D placement and manipulation of a virtual probe in a 3D environment, according to an embodiment of the present teaching.

FIG. 13 depicts another construct of an exemplary system 1300 that facilitates the placement and manipulation of a virtual surgical instrument and a treatment zone in a 3D environment for percutaneous pre-operational surgical planning, according to an embodiment of the present teaching. It is noted that the same mechanisms and modules that have been described above with respect to FIG. 12 will not be repeated in this embodiment. In addition to the same mechanisms and modules in FIG. 12, the system 1300 further includes a treatment zone calculation module 1305, a treatment zone rendering mechanism 1310, and a control handling module 1315.

The treatment zone calculation module 1305 is configured to estimate a treatment zone caused by a surgical instrument (e.g., a probe). In this embodiment, the treatment zone is caused by the thermal energy of a probe. The 3D pose of the probe, the setting of the probe, such as the model, length, and level of thermal energy, and the thermal dissipation effects on the target organ and surrounding anatomic structure may be taken into account by a thermal dissipation model used by the treatment zone calculation module 1305 to estimate the affected 3D zone. The treatment zone rendering mechanism 1310 is configured to visualize the estimated 3D treatment zone in the 3D volume on the display screen 1210. In this embodiment, the visualization of the 3D treatment zone may be achieved in the same manner as described above for rendering the 3D objects and 3D virtual probe by the 3D scene rendering mechanism 1255 and the probe rendering mechanism 1250. The 3D treatment zone may be rendered together with the 3D objects and the 3D virtual probe in the 3D volume on the display screen 120 so that users can easily see the spatial relationships between them.

Figure 15A:
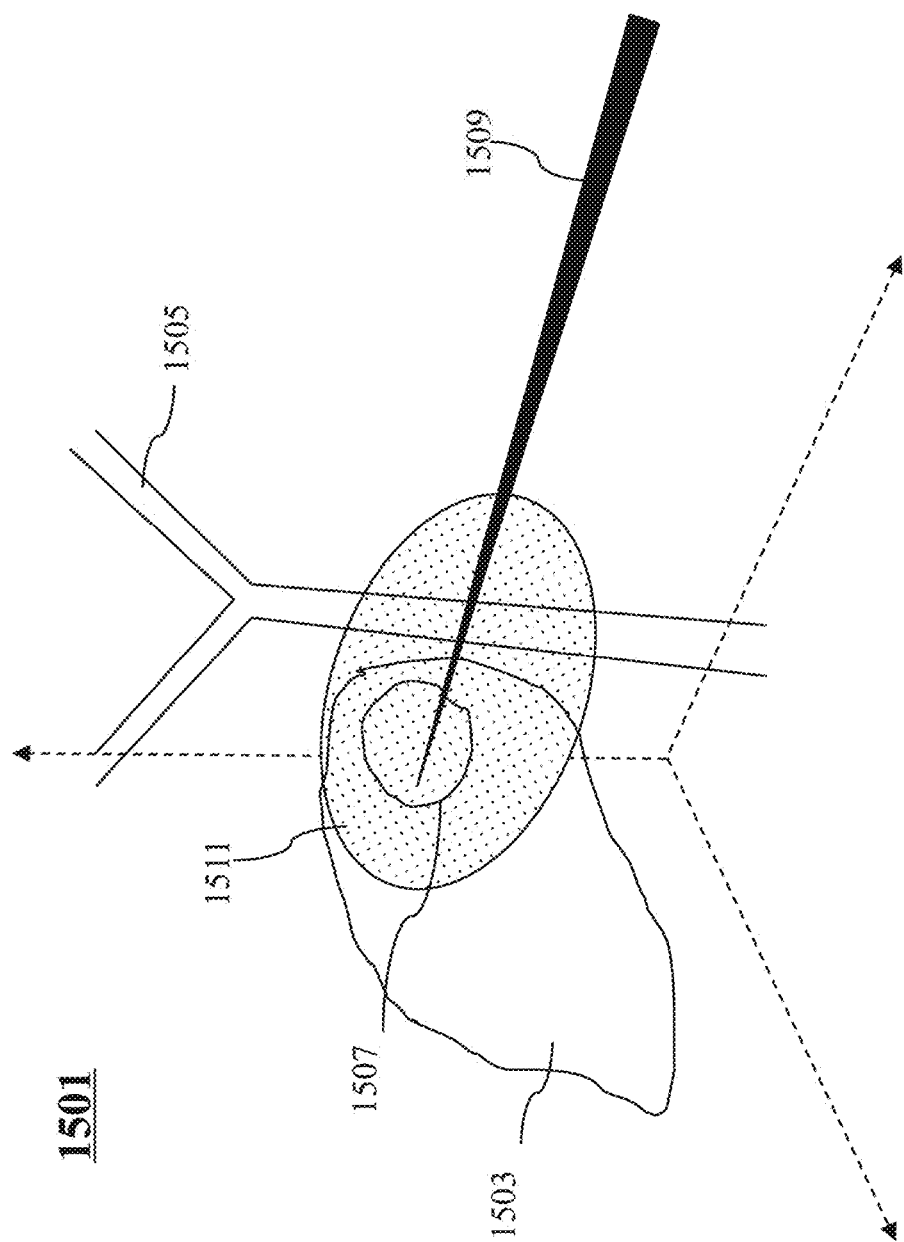
FIGS. 15(a)-15(b) depict 3D representations of a surgical instrument, an organ, anatomical structures, and a treatment zone in a 3D volume, according to an embodiment of the present teaching.
Figure 15B:
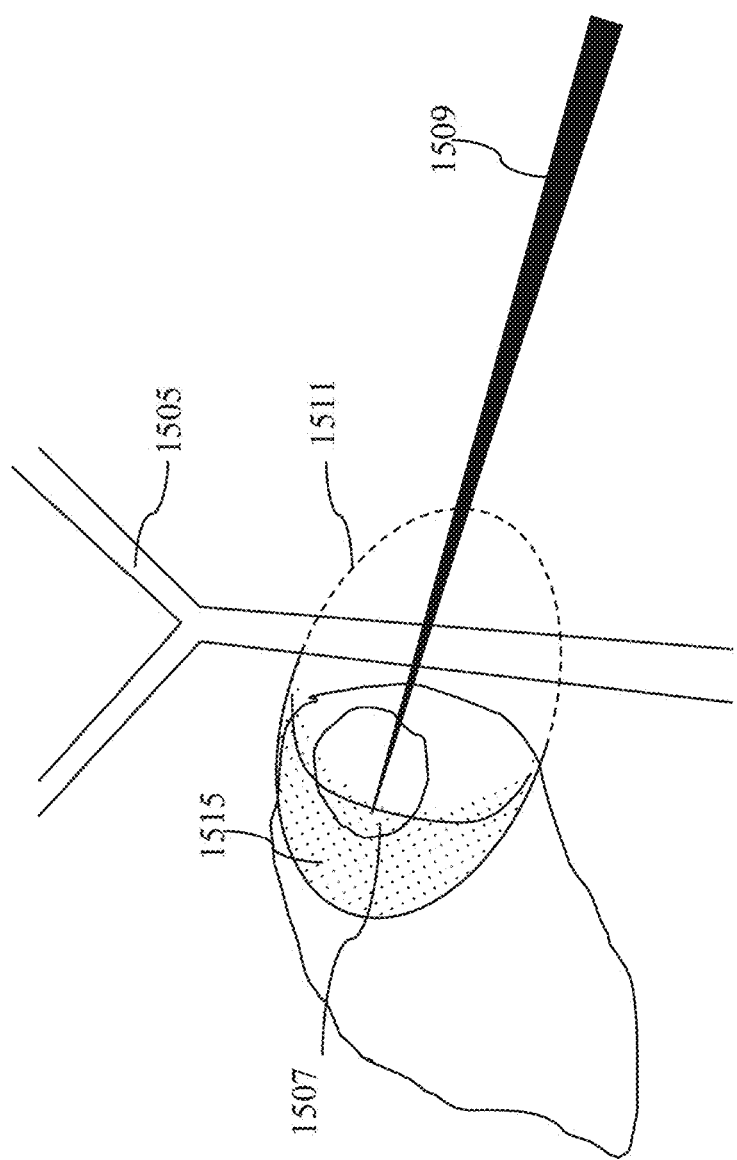

FIG. 15(*a*) shows that a 3D volume 1501 contains 3D objects corresponding to a target organ 1503 and surrounding anatomical structures 1505. A target area to be treated 1507 is inside the target organ 1503, which is surrounded by vascular structures 1507 nearby. A virtual probe 1509 is inserted into the target area 1507. Based on the 3D pose and setting of the probe, a corresponding treatment zone 1511 is estimated and visualized in the 3D volume 1501.

FIG. 15(*b*) shows the impact on the size and shape treatment zone caused by the thermal dissipation effect of the anatomical structures. In this example, the vascular structures 1507 dissipates heat from the probe 1509 through the vascular tree and thus, changes the size and shape of the treatment zone. So the original treatment zone 1511 is adjusted to an adjusted treatment zone 1515, which may not cover the target area 1507 completely and thus, make the treatment ineffective. In view of the visualization of the adjusted treatment zone 1515, a user may adjust the 3D pose and/or setting of the virtual probe 1509 accordingly in real-time to obtain an adjusted surgical plan for better treatment.

Returning to FIG. 13, the control handling module 1315 may provide one or more on-probe controls associated with the 3D virtual probe and/or one or more on-zone controls associated with the 3D treatment zone. The on-probe controls may be any graphic user interface elements such as a button, knob, scroll, etc. The setting of the probe that can be adjusted by the on-probe controls include, for example, the model of the probe, the length of the probe, and the level of thermal energy of the probe. The setting of the probe may be dynamically adjusted by a user via the on-probe control in-real time by manipulating the on-probe control in 3D. As a result, the 3D treatment zone may be dynamically adjusted accordingly based on the adjustment of the probe setting, and the adjusted 3D treatment zone is visualized in real-time in 3D.

The on-zone controls may be any graphic user interface elements provided on the 3D treatment zone itself (e.g., placed on the border or edge of the 3D treatment zone) for adjusting the length, radius-width, and pre-gap size of the treatment zone. When users move the mouse to one of the on-zone locations of the treatment zone, they can activate a corresponding on-zone control such as for resizing the zone. That is, the size and/or shape of the 3D treatment zone may be dynamically adjusted by a user via the on-zone controls. In some embodiments, based on the adjusted 3D treatment zone, the treatment zone calculation module 1305 may provide the adjusted setting of the probe. For example, when the user manipulate the on-zone control to increase the size of the 3D treatment zone to completely cover the target area of the organ, the level of thermal energy needed for enlarging the 3D treatment zone may be calculated and provide the user for reference.

Figure 16:
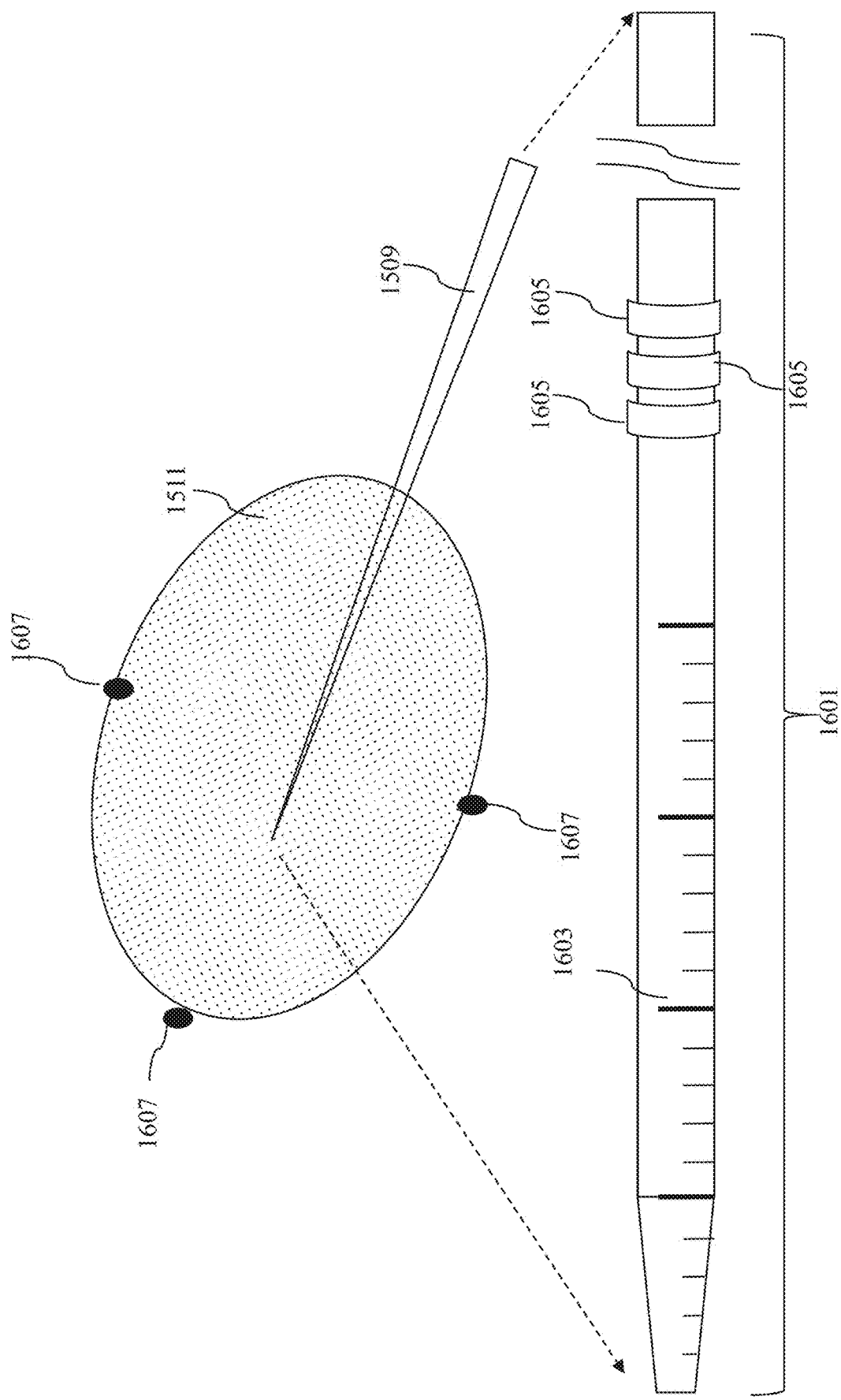
FIG. 16 depicts a plurality of controls associated with 3D representations of a surgical instrument and a treatment zone, according to an embodiment of the present teaching.

FIG. 16 shows a zoomed section 1601 of the probe 1509. It contains a scale 1603 and on-probe controls 1605. The scale 1603 enables a user to determine the required length of the probe 1509 visually and directly in 3D scene. The on-probe controls 1605 enable a user to adjust the treatment zone 1511. These controls 1605 may be used by a user to adjust the setting of the probe 1509 in parametric space and reflect the change of the treatment zone 1511 and/or probe 1509 spatially and visually in 3D scene in real-time. In this example, on-zone controls 1607 are provided on the border of the treatment zone 1611 to enable a user to adjust the size and/or shape of the treatment zone 1511 directly in spatial space.

Figure 14:
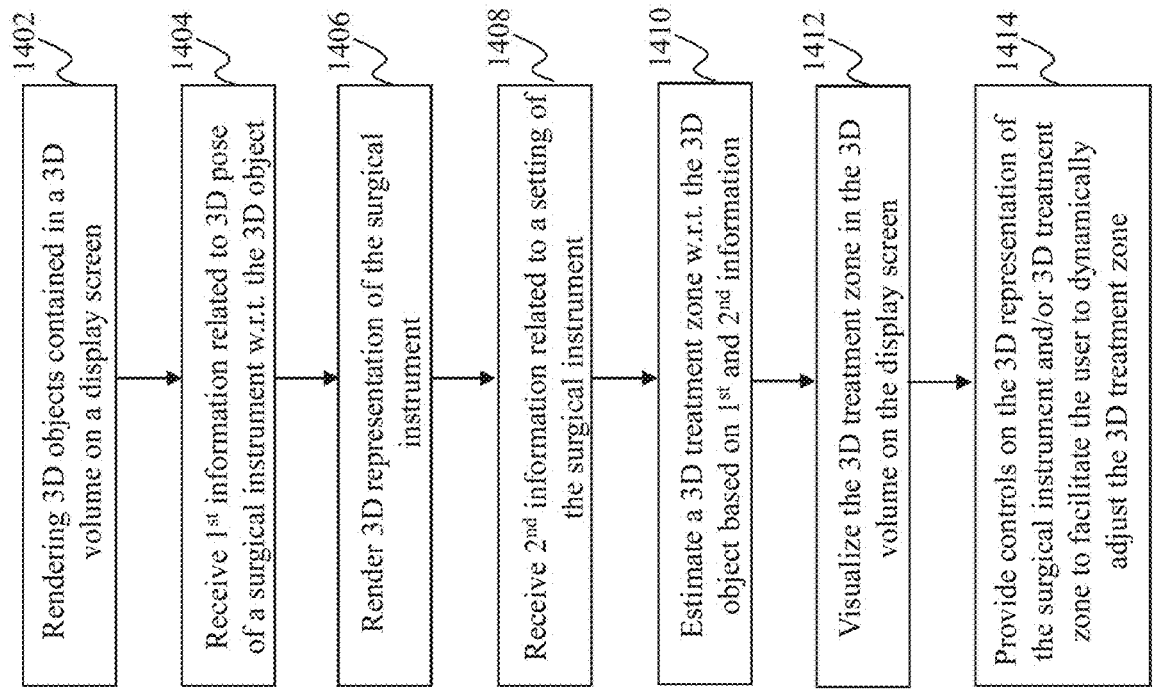
FIG. 14 is a flowchart of an exemplary process, in which a 3D treatment zone is estimated, adjusted, and rendered based on information specified by a user, according to an embodiment of the present teaching.

FIG. 14 is a flowchart of an exemplary process, in which a 3D treatment zone is estimated, adjusted, and rendered based on information specified by a user, according to an embodiment of the present teaching. At 1402, 3D objects contained in a 3D volume are rendered on a display screen. The 3D objects include a first 3D object corresponding to an organ and a second 3D object corresponding to an anatomical structure. At 1404, first information related to a 3D pose of a surgical instrument (e.g., a probe or a needle) with respect to the 3D objects is received from a user. At 1406, a 3D representation of the surgical instrument is rendered in the 3D volume based on the first information. At 1408, second information related to a setting of the surgical instrument is received from the user. The setting includes, for example, a model, length, and level of thermal energy of the surgical instrument. At 1410, a 3D treatment zone in the 3D volume with respect to the 3D objects is estimated based on the first and second information. In one embodiment, the 3D treatment zone may be estimated further based on a thermal dissipation effect on the second 3D object corresponding to the anatomical structure. At 1412, the 3D treatment zone is visualized in the 3D volume on the display screen. The 3D representation of the surgical instrument and the 3D treatment zone are to be used for surgical procedure planning.

At 1414, one or more controls associated with the 3D representation of the surgical instrument and/or the 3D treatment zone are provided to facilitate the user to dynamically adjust the 3D treatment zone. In one example, a first set of controls associated with the 3D representation of the surgical instrument may be provided. The setting of the surgical instrument can be dynamically updated by the user via the first set of controls. In another example, a second set of controls associated with the 3D treatment zone may be provided. The 3D treatment zone can be dynamically adjusted by the user via the second set of controls. Additionally or optionally, an update of the second information related to the setting of the surgical instrument may be determined based on the adjusted 3D treatment zone and provided to the user.

To implement various modules, units, and their functionalities described in the present disclosure, computer hardware platforms may be used as the hardware platform(s) for one or more of the elements described herein (e.g., the system 1300 described with respect to FIGS. 1-16). The hardware elements, operating systems and programming languages of such computers are conventional in nature, and it is presumed that those skilled in the art are adequately familiar therewith to adapt those technologies to surgical procedure planning as described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result the drawings should be self-explanatory.

Figure 17:
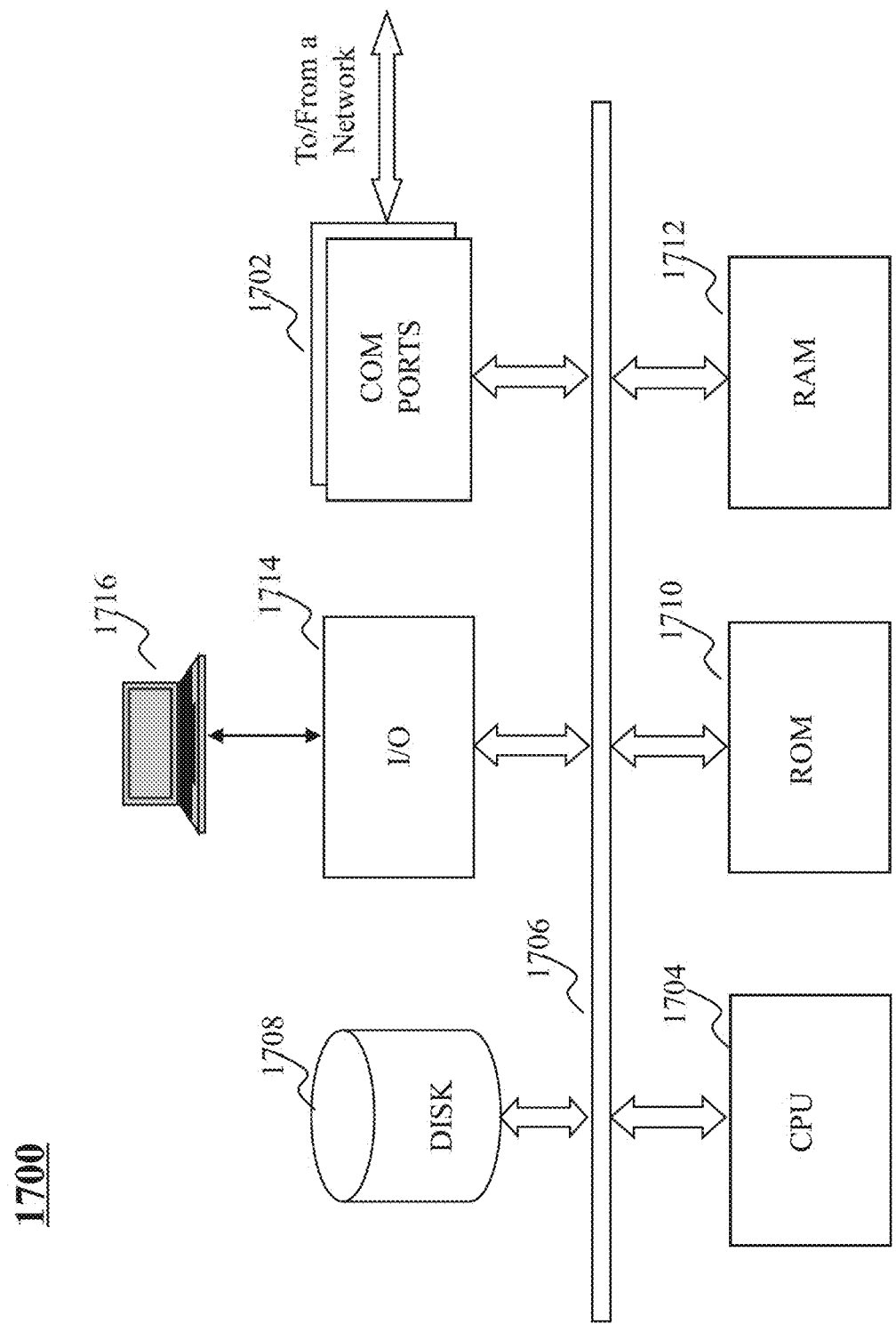
FIG. 17 depicts the architecture of a computer which can be used to implement a specialized system incorporating the present teaching.

FIG. 17 depicts the architecture of a computing device which can be used to realize a specialized system implementing the present teaching. Such a specialized system incorporating the present teaching has a functional block diagram illustration of a hardware platform which includes user interface elements. The computer may be a general purpose computer or a special purpose computer. Both can be used to implement a specialized system for the present teaching. This computer 1700 may be used to implement any component of surgical procedure planning techniques, as described herein. For example, the system 1300 may be implemented on a computer such as computer 1700, via its hardware, software program, firmware, or a combination thereof. Although only one such computer is shown, for convenience, the computer functions relating to surgical procedure planning as described herein may be implemented in a distributed fashion on a number of similar platforms, to distribute the processing load.

The computer 1700, for example, includes COM ports 1702 connected to and from a network connected thereto to facilitate data communications. The computer 1700 also includes a central processing unit (CPU) 1704, in the form of one or more processors, for executing program instructions. The exemplary computer platform includes an internal communication bus 1706, program storage and data storage of different forms, e.g., disk 1708, read only memory (ROM) 1710, or random access memory (RAM) 1712, for various data files to be processed and/or communicated by the computer, as well as possibly program instructions to be executed by the CPU 1704. The computer 1700 also includes an I/O component 1714, supporting input/output flows between the computer and other components therein such as user interface elements 1716. The computer 1700 may also receive programming and data via network communications.

Hence, aspects of the methods of surgical procedure planning and/or other processes, as outlined above, may be embodied in programming Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described above may be embodied in a hardware device, it may also be implemented as a software only solution—e.g., an installation on an existing server. In addition, the surgical procedure planning system as disclosed herein may be implemented as a firmware, firmware/software combination, firmware/hardware combination, or a hardware/firmware/software combination.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

We claim:

1. A method, implemented on a computing device having at least one processor, storage, and a communication platform capable of connecting to a network for surgical procedure planning, the method comprising:
   rendering at least one three dimensional (3D) object contained in a 3D volume on a display screen, wherein the at least one 3D object includes a 3D object corresponding to an organ;
   receiving, from a user, first information related to a 3D pose of a surgical instrument positioned with respect to the at least one 3D object;
   rendering a 3D representation of the surgical instrument in the 3D volume based on the first information;
   receiving, from the user, second information related to a setting of the surgical instrument;
   estimating a 3D treatment zone in the 3D volume with respect to the at least one 3D object based on the first and second information;
   visualizing the 3D treatment zone in the 3D volume on the display screen, wherein the 3D representation of the surgical instrument and the 3D treatment zone are to be used for surgical procedure planning; and
   providing, in the 3D volume, one or more controls directly embedded on a surface of the 3D representation of the surgical instrument and one or more controls directly embedded on a boundary of the 3D treatment zone, wherein the one or more controls directly embedded on a surface of the 3D representation of the surgical instrument facilitate the user to dynamically adjust the setting of the surgical instrument including a model of the surgical instrument so as to indirectly change the 3D treatment zone, and the one or more controls directly embedded on a boundary of the 3D treatment zone facilitate the user to dynamically adjust at least shape or size of the 3D treatment zone.

2. The method of claim 1, wherein the at least one 3D object further includes another 3D object corresponding to an anatomical structure.

3. The method of claim 2, wherein the 3D treatment zone is estimated further based on a thermal dissipation effect on the other 3D object.

4. The method of claim 1, wherein providing one or more controls comprises:

providing a first set of controls associated with the 3D representation of the surgical instrument to facilitate the user to dynamically update the setting of the surgical instrument via the first set of controls.

5. The method of claim 4, wherein the setting further includes at least one of:
a length of the surgical instrument; and
a level of thermal energy of the surgical instrument.

6. The method of claim 1, further comprising:
determining an update of the second information based on the adjusted 3D treatment zone; and
providing the update of the second information to the user.

7. The method of claim 1, wherein the one or more controls directly embedded on the surface of the 3D representation of the surgical instrument facilitate the user to adjust a pose of the surgical instrument.

8. A system for surgical procedure planning, comprising:
a three dimensional (3D) scene rendering unit implemented by a processor and configured for rendering at least one 3D object contained in a 3D volume on a display screen, wherein the at least one 3D object includes a 3D object corresponding to an organ;
a probe handling unit implemented by the processor and configured for receiving, from a user, first information related to a 3D pose of a surgical instrument positioned with respect to the at least one 3D object;
a probe rendering unit implemented by the processor and configured for rendering a 3D representation of the surgical instrument in the 3D volume based on the first information;
a control handling unit implemented by the processor and configured for receiving, from the user, second information related to a setting of the surgical instrument;
a treatment zone calculation unit implemented by the processor and configured for estimating a 3D treatment zone in the 3D volume with respect to the at least one 3D object based on the first and second information; and
a treatment zone rendering unit implemented by the processor and configured for visualizing the 3D treatment zone in the 3D volume on the display screen, wherein the 3D representation of the surgical instrument and the 3D treatment zone are to be used for surgical procedure planning, wherein
the control handling unit is further configured for providing, in the 3D volume, one or more controls directly embedded on a surface of the 3D representation of the surgical instrument and one or more controls directly embedded on a boundary of the 3D treatment zone, wherein the one or more controls directly embedded on a surface of the 3D representation of the surgical instrument facilitate the user to dynamically adjust the setting of the surgical instrument including a model of the surgical instrument so as to indirectly change the 3D treatment zone, and the one or more controls directly embedded on a boundary of the 3D treatment zone facilitate the user to dynamically adjust at least shape or size of the 3D treatment zone.

9. The system of claim 8, wherein the at least one 3D object further includes another 3D object corresponding to an anatomical structure.

10. The system of claim 9, wherein the 3D treatment zone is estimated further based on a thermal dissipation effect on the other 3D object.

11. The system of claim 8, wherein the control handling unit is further configured for providing a first set of controls associated with the 3D representation of the surgical instrument to facilitate the user to dynamically update the setting of the surgical instrument via the first set of controls.

12. The system of claim 11, wherein the setting further includes at least one of:
a length of the surgical instrument; and
a level of thermal energy of the surgical instrument.

13. The system of claim 8, wherein the treatment zone calculation unit is further configured for:
determining an update of the second information based on the adjusted 3D treatment zone; and
providing the update of the second information to the user.

14. A non-transitory machine readable medium having information recorded thereon for surgical procedure planning, wherein the information, when read by a machine, causes the machine to perform the steps of:
rendering at least one three dimensional (3D) object contained in a 3D volume on a display screen, wherein the at least one 3D object includes a 3D object corresponding to an organ;
receiving, from a user, first information related to a 3D pose of a surgical instrument positioned with respect to the at least one 3D object;
rendering a 3D representation of the surgical instrument in the 3D volume based on the first information;
receiving, from the user, second information related to a setting of the surgical instrument;
estimating a 3D treatment zone in the 3D volume with respect to the at least one 3D object based on the first and second information;
visualizing the 3D treatment zone in the 3D volume on the display screen, wherein the 3D representation of the surgical instrument and the 3D treatment zone are to be used for surgical procedure planning; and
providing, in the 3D volume, one or more controls directly embedded on a surface of the 3D representation of the surgical instrument and one or more controls directly embedded on a boundary of the 3D treatment zone, wherein the one or more controls directly embedded on a surface of the 3D representation of the surgical instrument facilitate the user to dynamically adjust the setting of the surgical instrument including a model of the surgical instrument so as to indirectly change the 3D treatment zone, and the one or more controls directly embedded on a boundary of the 3D treatment zone facilitate the user to dynamically adjust at least shape or size of the 3D treatment zone.

15. The medium of claim 14, wherein the at least one 3D object further includes another 3D object corresponding to an anatomical structure.

16. The medium of claim 15, wherein the 3D treatment zone is estimated further based on a thermal dissipation effect on the other 3D object.

17. The medium of claim 14, wherein the setting further includes at least one of:
a length of the surgical instrument; and
a level of thermal energy of the surgical instrument.

18. The medium of claim 14, further comprising:
determining an update of the second information based on the adjusted 3D treatment zone; and
providing the update of the second information to the user.

* * * * *